United States Patent [19]

Fogarty et al.

[11] Patent Number: 5,601,589
[45] Date of Patent: Feb. 11, 1997

[54] EXTRALUMINAL BALLOON DISSECTION APPARATUS AND METHOD

[75] Inventors: Thomas J. Fogarty, Portola Valley; George D. Hermann, Los Gatos; Jan M. Echeverry, San Jose, all of Calif.

[73] Assignee: General Surgical Innovations, Inc., Palo Alto, Calif.

[21] Appl. No.: 267,484

[22] Filed: Jun. 29, 1994

[51] Int. Cl.$^6$ ............................. A61M 29/00; A61M 5/00
[52] U.S. Cl. ........................ 606/192; 604/103; 600/207
[58] Field of Search ........................ 128/20, 116; 606/1, 606/119, 151, 190–200; 604/96, 97, 103, 104, 164, 170, 174, 264; 600/201, 204, 207

[56] References Cited

U.S. PATENT DOCUMENTS

| | | |
|---|---|---|
| 4,493,711 | 1/1985 | Chin et al. . |
| 4,779,611 | 10/1988 | Groters et al. ........................ 600/116 |
| 5,188,630 | 2/1993 | Christoudias ........................ 606/1 |
| 5,269,753 | 12/1993 | Wilk ........................ 606/192 |
| 5,346,504 | 9/1994 | Ortiz et al. ........................ 600/116 |
| 5,359,995 | 11/1994 | Sewell ........................ 606/192 |
| 5,383,889 | 1/1995 | Warner et al. ........................ 606/192 |
| 5,391,178 | 2/1995 | Yapor ........................ 606/192 |
| 5,425,357 | 6/1995 | Moll et al. ........................ 606/192 |

OTHER PUBLICATIONS

Lam, et al., "Surgical Procedures for Uncomplicated (Routine) Female Stress Incontinence." Urologic Clinics of North America—vol. 18, No. 2, May 1991.

*Primary Examiner*—Glenn Dawson
*Attorney, Agent, or Firm*—Lyon & Lyon

[57] ABSTRACT

A balloon dissection apparatus for forming an anatomic working space alongside an elongate vessel in a body having a tunneling shaft having proximal and distal extremities. A flexible elongate substantially cylindrical balloon is carried by the tunneling shaft and has proximal and distal extremities. The balloon has at least a portion of the distal extremity folded inwardly into the balloon to shorten the length of the balloon so that the folded balloon has a length which is not substantially greater than the length of the tunneling shaft. An inflation tube is coupled to the balloon for inflating the balloon to cause the distal folded extremity to evert and roll outwardly to provide an inflated balloon having a length greater than the length of the tunneling shaft.

8 Claims, 2 Drawing Sheets

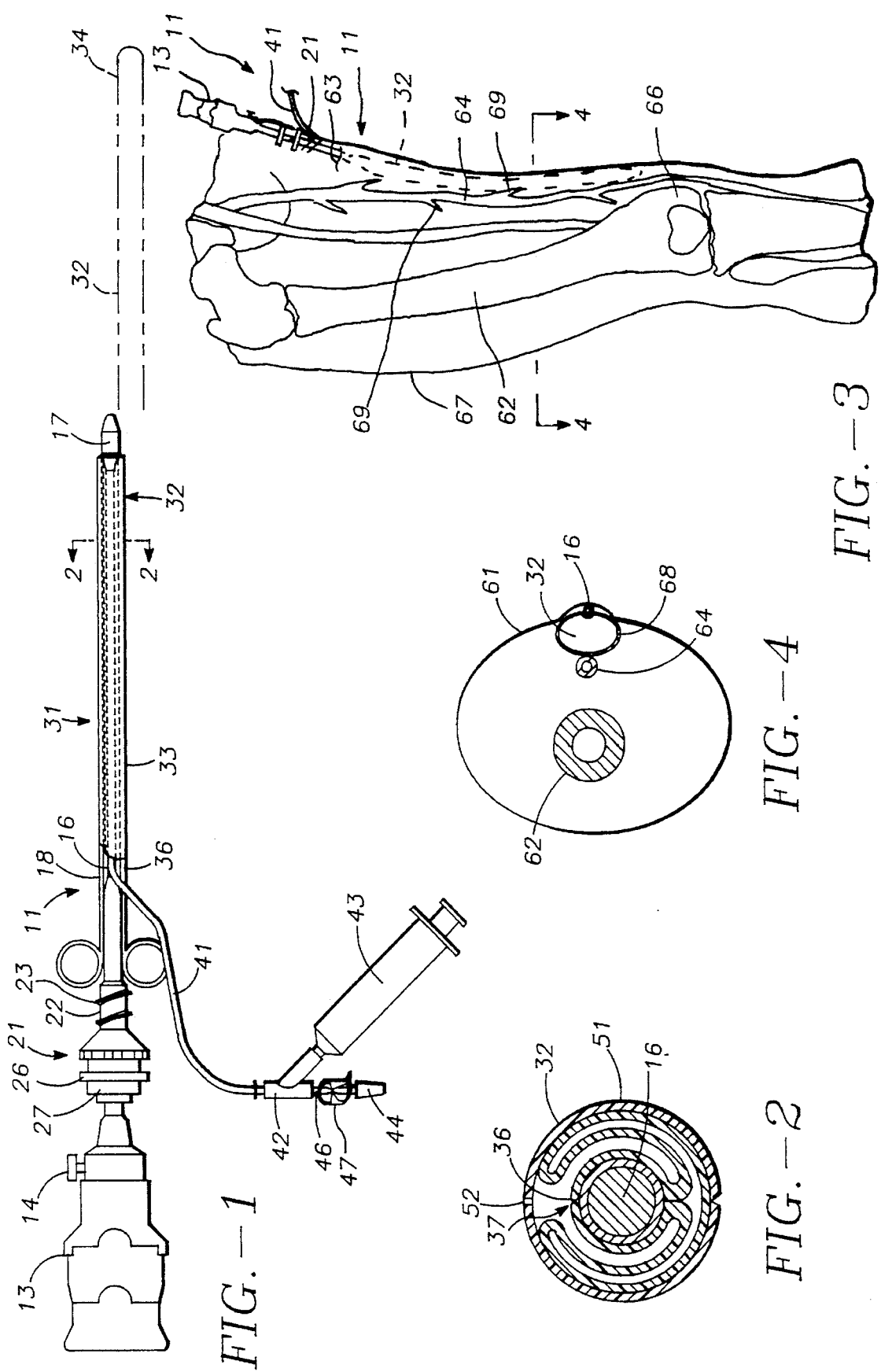

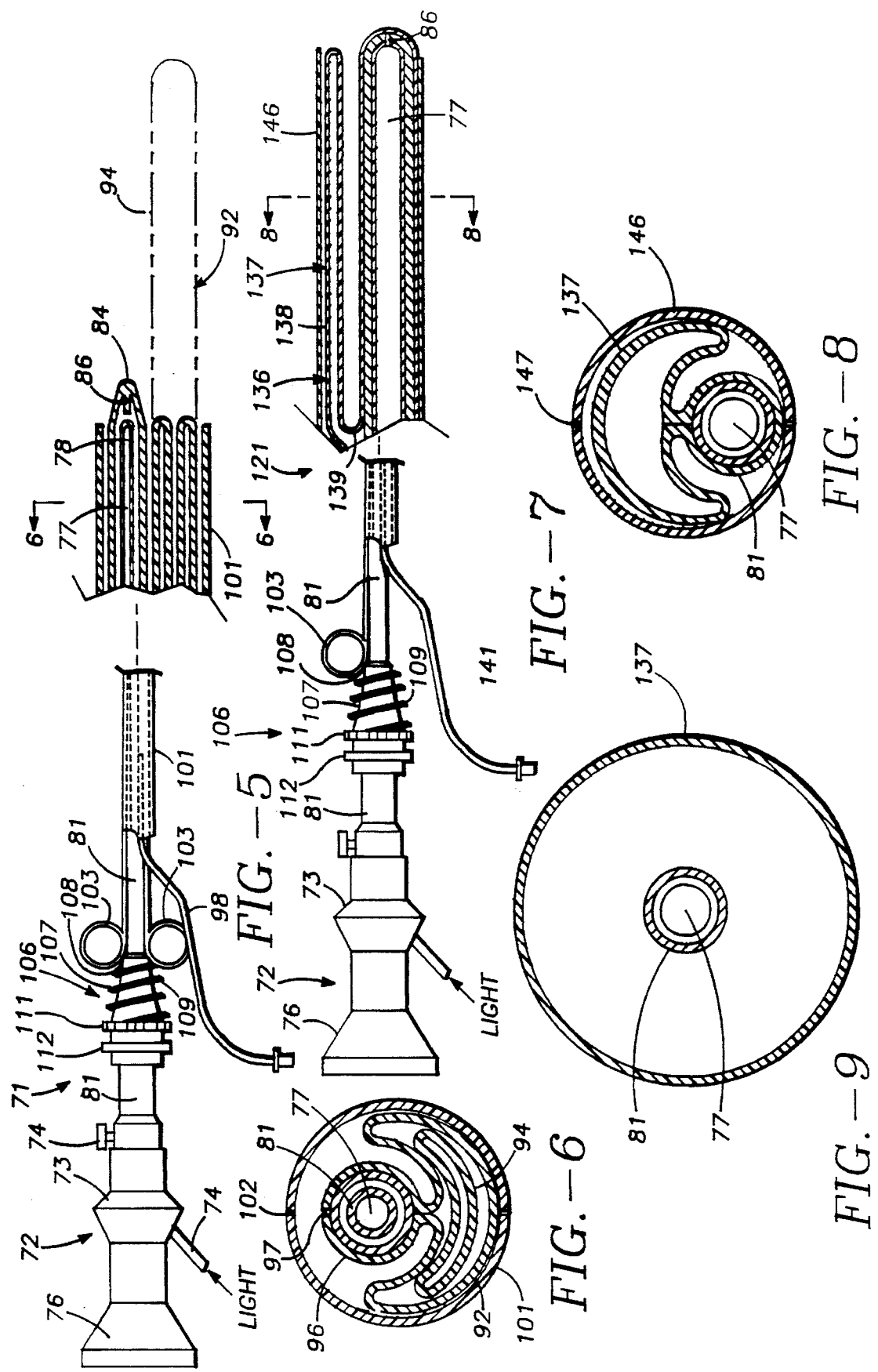

EXTRALUMINAL BALLOON DISSECTION APPARATUS AND METHOD

This invention relates to an extraluminal balloon dissection apparatus and method, and more particularly to such a vascular method and apparatus which can be used for forming an anatomic working space alongside an elongate vessel and particularly a peripheral vessel.

In co-pending application Ser. No. 07/893,988 filed on Jun. 2, 1992, there is disclosed an apparatus and method for developing an anatomic space for laparoscopic procedures which includes a balloon dissection apparatus for use in laparoscopic procedures. In co-pending application Ser. No. 08/267,488 filed Jun. 29, 1994 there are disclosed further improvements in the apparatus and method for developing anatomic space for use in laparoscopic procedures. In the apparatus and method therein disclosed, the balloon dissection apparatus includes relatively large-area balloons which expand laterally which are not particularly adapted for surgical procedures on elongate vessels. There is therefore a need for a new and improved balloon dissection apparatus and method.

In general it is an object of the invention is to provide an apparatus and method which is particularly adapted for use with elongate vessels and particularly peripheral vessels.

Another object of the invention is to provide an apparatus and method which is particularly suitable for harvesting the saphenous vein for use in heart bypass operations.

Another object of the invention is to provide an apparatus and method which is particularly suitable for use in in situ saphenous vein bypass procedures.

Another object of the invention is to provide an apparatus and method in which such a procedure can be accomplished with a reduced number of incisions.

Another object of the invention is to provide an apparatus and method of the above character in which tunneling along the side of the vessel is used.

Another object of the invention is to provide an apparatus and method of the above character in which a reduced number of incisions are required.

Another object of the invention is to provide an apparatus and method of the above character which is minimally invasive.

Another object of the invention is to provide an apparatus and method of the above character in which the procedures can be viewed continuously through a laparoscope or other video based endoscope.

Another object of the invention is to provide an apparatus and method of the above character in which it is possible to dissect along a naturally existing path alongside a vessel to perform various surgical procedures.

Another object of the invention is to provide an apparatus and method of the above character which utilizes a tunneling shaft and a balloon which makes it possible for the balloon to tunnel a distance which is substantially twice the length of the tunneling shaft.

Additional objects and features of the invention will appear from the following description in which the preferred embodiments are set forth in detail in conjunction with the accompanying drawings.

FIG. 1 is a side elevational view of a balloon dissection apparatus incorporating the present invention.

FIG. 2 is a cross-sectional view taken along the line 2—2 of FIG. 1.

FIG. 3 is an illustration showing the manner in which the apparatus and method of the present would be utilized for performing an in situ saphenous vein bypass procedure.

FIG. 4 is a cross-sectional view taken along the line 4—4 of FIG. 3.

FIG. 5 is a side elevational view of another embodiment of an apparatus incorporating the present invention.

FIG. 6 is a cross-sectional view taken along the line 6—6 of FIG. 5.

FIG. 7 is a side elevational view of still another embodiment of an apparatus incorporating the present invention.

FIG. 8 is a cross-sectional view taken along the line 8—8 of FIG. 7.

FIG. 9 is a cross-sectional view showing the dissection balloon in FIG. 8 in an inflated condition.

In general, the extraluminal balloon dissection apparatus is comprised of a tunneling shaft. An elongate balloon is carried by the tunneling shaft and has proximal and distal extremities. The balloon has at least a portion of the distal extremity folded inwardly into the balloon. A balloon cover encloses the balloon carried by the tunneling shaft and holds it in a collapsed condition against the shaft.

More in particular, as shown in the FIGS. 1–4 of the drawings the balloon dissection apparatus for use extraluminal balloon dissection, consists of a tunneling shaft assembly 12 of the type described in co-pending application Ser. No. 08/267,488 filed Jun. 29, 1994. As disclosed therein, the tunneling shaft assembly is comprised of a three-part handle assembly 13 having an inflation fitting 14 thereon and which has a tunneling rod or shaft or guide rod or shaft 16 mounted thereon. The tunneling rod 16 has an olive-shaped obturator tip 17 mounted on the distal extremity thereof. The tunneling shaft extends through a cannula 18 secured to one part of the three-part handle assembly 13. A skin seal 21 is slidably mounted and frictionally retained on the cannula 21 secured to and forming a part of the handle assembly 13 and is provided with a cylindrical surface 22 on which there are provided helical threads 23. A housing 26 adjoins the cylindrical surface 22 and is provided with a duckbill valve (not shown) therein. A collar 28 is axially mounted on the housing 26 for moving the skin seal 21 between slidable and fixed positions on the cannula 18.

A balloon assembly 31 is carried by the tunneling rod 16 and consists of a balloon 32 which is provided with proximal and distal extremities 33 and 34. The balloon 32 is cylindrical and elongate and can be referred to as having a "hot dog" shape. Typically, the balloon 32 is formed of a non-elastic material such as a polyethylene. Typically, the balloon 32 has a length which is substantially greater than the length of the tunneling rod 16 for a purpose hereinafter described.

In order to facilitate insertion of the balloon 32 during a dissection procedure as hereinafter described, the distal extremity 34 is folded inwardly into the balloon 32 to thereby shorten the length of the balloon so that the folded balloon has a distal extremity which does not extend substantially beyond the distal extremity of the tunneling rod 16 or, in other words, the tip 17, as shown in FIG. 1. Thus, as shown in FIG. 1, the distal extremity can be folded inwardly so that approximately one-half of the balloon has been folded into the other one-half of the balloon to provide a balloon which is approximately one-half its extended length. It should be appreciated that if it is desired to provide a still shorter folded balloon, it is possible to again fold the balloon by bringing the folded distal extremity inwardly again to, in effect, shorten the balloon so it is only approximately one-quarter of its original length.

The balloon assembly 31 also includes means for releasably securing the balloon 32 to the tunneling rod 16 and, as shown, consists of sleeve 36 which can be formed of the same material as the balloon 32 which can be formed integral with the balloon 32 or be formed separately from the balloon and secured thereto by suitable means such as an adhesive. The sleeve has a length so it extends substantially the entire length of the tunneling rod and circumscribes the tunneling rod. The sleeve 36 is provided with a weakened region 37 extending the length thereof which can be formed in a suitable manner, as for example by providing perforations therein extending axially of the sleeve so that the sleeve 36 can be separated from the tunneling rod when it is desired to remove the tunneling rod 16 as hereinafter described.

The balloon assembly 31 also includes means for inflating the balloon 32 in the form of a flexible tubular member 41 which has its distal extremity embedded within the balloon 39 so that it is open to the interior of the balloon. A "wye" adapter 42 is secured to the proximal extremity of the tubular member 41 and has a hand-operated syringe 43 removably mounted therein which can be utilized for inflating the balloon 32 with a suitable fluid, as for example a saline solution. The "wye" adapter 42 is also connected to another fitting 44 by another tube 46 which has a close-off clamp 47 mounted thereon.

A tubular balloon cover 51 is provided of the type described in co-pending application Ser. No. 08/267,488 filed, Jun. 29, 1994, which is adapted to press the collapsed balloon 32 about the tunneling rod 16. The balloon cover 51 is provided with a weakened region 52 extending the length thereof so that the balloon cover can be separated from the balloon and the tunneling shaft when it is desired to inflate the balloon. Alternatively, the balloon 32 can be packed into the balloon cover 51 without a guide rod 16.

Operation and use of the balloon dissection apparatus 11 may now be utilized in connection with the extraluminal balloon dissection procedure of the present invention. Let it be assumed that it is desired to perform an in situ saphenous vein bypass to improve the circulation of arterial blood into the leg 61 of a patient having a femur 62 therein. The procedure, in many respects, is similar to that described in co-pending application Ser. No. 08/267,488 filed Jun. 29, 1994. As described therein, an incision 63 can be made in the groin in the thigh of the leg 61 immediately adjacent the saphenous vein to serve as the bypass. The olive tip 17 of the balloon dissection apparatus 11 is then introduced through the groin incision 63 and the tip 17 is advanced along the saphenous vein 64 between the saphenous vein and the skin as shown in FIG. 3 until the tunneling rod 16 and the balloon assembly 31 are disposed within the leg 61 adjacent the saphenous vein 64. It should be appreciated if desired dissection can be accomplished along the saphenous vein 64 on the side away from the skin. As soon as dissection has been accomplished, the balloon cover 51 is removed with a finger of the hand, causing the balloon cover 51 to separate along the weakened region 52 and to leave in place on the tunneling rod or shaft 16 the balloon 32. The balloon 32 is then progressively inflated by introducing a fluid such as a saline solution through the syringe 43. As the balloon 32 begins to inflate, the distal extremity 34 of the balloon will begin to unroll or, in other words, evert or propagate in a direction downwardly of the leg toward and beyond the knee 66 until the distal extremity 34 is fully distended, as shown in dotted lines in FIG. 3.

After the balloon 32 has been completely inflated and distended, the balloon 32 can be deflated by opening the clamp 47. After the balloon has been deflated, the entire balloon assembly 31 can be removed through the incision by stripping the sleeve 36 from the tunneling shaft assembly 12 along the weakened region 37. The skin seal 21 can then be advanced into and threaded into the incision 63 to form a gas-tight seal with the skin 67 on the leg 61. Thereafter, an insufflation gas can be introduced through the fitting 14 carried by the handle 13 to the region which has been dissected by the balloon 32 to provide an anatomic space 68 extending lengthwise of the saphenous vein. The entire tunneling shaft assembly 12 can then be removed in the manner described in co-pending application Ser. No. 08/267, 488 filed Jun. 29, 1994, leaving the skin seal 21 in place with the housing 26 having the duckbill valve (not shown) therein to form a gas-tight seal after the tunneling shaft assembly 12 has been removed. The side branches 69 of the saphenous vein are exposed in the insufflated anatomic space 68 extending along the saphenous vein. Clips (not shown) can be applied to these side branches in either of two ways. In one way, an incision can be made at the distal extremity of the insufflated space by the use of a trocar and then introducing a clip applier through that trocar and then applying hemostats or clips to the side branches while the procedure is being viewed through a laparoscope introduced through the skin seal 21 from the groin area of the leg 61. In this manner, many of the side branches can have clips applied to the same with one incision in the groin and another incision below the knee to thereby greatly reduce the number of incisions required for clipping off the side branches of the saphenous vein.

Using this same insufflated space, the side branches can be clipped off by introducing an operating endoscope through the skin seal 21 and introducing a clip applier through the operating laparoscope to clip off the side branches while the procedure is being viewed through the laparoscope.

If it is desired to advance still further down the leg than that which can be accomplished with the first balloon dissection apparatus 11, a second balloon dissection apparatus can be introduced through the lowermost incision and the same procedure accomplished to dissect the saphenous vein down to the ankle of the leg of the patient. The same procedure then can be utilized for clipping off the side branches of that portion of the saphenous vein. After the clipping of the side branches has been completed, the upper portion of the saphenous vein can be connected through the first incision to the artery which the incision can be closed in the conventional manner. The lower incision can be utilized to connect the saphenous vein to another vein.

By utilizing such a procedure with the balloon dissection apparatus 11 of the present invention, it is possible to utilize moderate-sized incisions at the top of the leg and at the bottom of the leg and possibly one in the middle of the leg to thereby eliminate many of the incisions which are normally required to be made into the skin along the length of the leg of the patient in order to clip off or occlude the side branches of the saphenous vein. This makes it possible to greatly reduce the risk of infection from multiple incisions. The recovery time in the hospital is reduced. It also reduces the time required for completing the procedure. The recovery time for the patient and the pain which must be endured by the patient are greatly reduced.

The balloon dissection apparatus of the present invention can now also be utilized for harvesting the saphenous vein, as for example in a coronary artery bypass procedure. In the past, it has been necessary to make a full-length incision all the way down the leg of the patient having the bypass procedure performed to remove the saphenous vein. With the balloon dissection apparatus 11 of the present invention, it is possible to form an incision in the groin of the patient and then utilize the apparatus to dissect an anatomic working space adjacent the saphenous vein in the leg of the patient. This can be accomplished by introducing the balloon 32 by the use of the tunneling shaft assembly 12 alongside the saphenous vein 64 and thereafter inflating the balloon to cause it to evert to create a dissection of tissue along substantially the entire length of the saphenous vein of the patient to create an anatomic space. The balloon 32 is removed. The anatomic space is insufflated and additional trocars inserted into the dissected space. The saphenous vein side branches are exposed with some additional manual dissection and are clipped and transectd. The saphenous vein is dissected free from its surrounding tissue, the proximal and distal ends are clipped and transected and the saphenous vein is harvested through the incision. This approach drastically reduces the length of the incision which is normally required to harvest the saphenous vein. The saphenous vein can be pulled out through the incision and the side branches can then be closed on the operating table in a standard procedure. Similarly, valves within the saphenous vein can be removed in a conventional manner if that is desired.

In connection with the present invention, it is preferable to utilize a non-elastomeric balloon so that it is possible to control the shape of the dissected region. By way of example, for extraluminal procedures involving the saphenous veins, it is desirable to have a tunneling shaft having a length of approximately 12 inches with the balloon fully distended having a length of approximately 20–30 inches and a maximum diameter when inflated of approximately 1–3 inches. It should be appreciated that different sizes of balloons can be provided in accordance with the present invention to provide inflated diameters as great as 3–4 inches where that may be desired.

The inflation pressures for the balloon 32 generally are relatively low, as for example below one atmosphere. Alternatively, the balloons can be of a relatively small diameter, as for example 10 millimeters in diameter, where is it desired to tunnel down along the natural plane of an artery for the purpose of inserting a synthetic graft.

From the foregoing, it can be seen that the balloon dissection apparatus 11 is particularly suitable for the treatment of conduits or vessels using extraluminal procedures. The procedures are minimally invasive in that pathways are dissected which run along parallel to the vessel, as for example the artery or vein. The dissection occurs along a natural plane immediately adjacent to the vessel.

The dissecting balloon 32 will find its way along the vessel because that is a natural plane of separation permitting dissection to occur so that the balloon will naturally propagate in the desired direction along the vessel so that procedures can be performed in conjunction with or on the vessel.

In place of a rigid tunneling shaft assembly 12, it should be appreciated that a semi-rigid tunneling assembly can be provided giving some flexibility while providing enough rigidity to make possible a blunt dissection with the use of the olive-shaped tip 17 to facilitate the introduction of the balloon to a desired location alongside the vessel of interest. It also should be appreciated that such a balloon dissection apparatus can be utilized in conjunction with other vessels in the human body, as for example for gaining access along the esophagus, carotid arteries, brain drain shunts, and nerves. The principal thrust of the present invention is to provide a balloon dissection apparatus in which the balloon is capable of dissecting along a region that follows a natural existing path along a vessel such as an artery, a vein, a lymphatic vessel, a trachea or an esophagus, or even a nerve bundle.

Another embodiment of a balloon dissection apparatus incorporating the present invention is provided by the apparatus 71 as shown in FIGS. 5 and 6. In this embodiment of the invention, the apparatus 71 includes a laparoscope or endoscope 72 of a conventional type which is provided with a housing 73 carrying a light inlet fitting 74 and having an eyepiece 76 carried thereby. A probe 77 is mounted on the housing 73 and has a distal extremity 78. The distal extremity can have a suitable viewing angle, as for example a straight viewing angle which is parallel to the axis of the probe 77 or an angle of 30° with respect to the longitudinal axis. As is well known to those skilled in the art, such a laparoscope is provided with optical means for receiving light from the fitting 74 and passing it through the distal extremity so that light is available for viewing through the eyepiece 76.

In accordance with the present invention, the balloon dissection apparatus 71 may include the use of an elongate cylindrical or tubular cover 81 which can be characterized as a scope cover. The cover 81 can be of the type described in co-pending application Ser. No. 08/267,488 filed Jun. 29, 1994, and is formed of a suitable transparent material such as a clear polycarbonate. The cover 81 is in the form of an elongate tubular member 82 which has a bore 83 extending therethrough which is sized so that it can readily accommodate the probe 77 of the laparoscope 72. It also has a length so that it can extend the entire length of the probe. A rounded, hemispherical tip 84 is provided on the distal extremity of the tubular member 82 and can be formed integral therewith, as shown, or alternatively, if desired, it can be formed as a separate piece which is bonded by suitable means such as an adhesive (not shown) to the tubular member 82. The tip 84, in accordance with the present invention, is also formed of a transparent material such as a clear polycarbonate, hereinbefore described, to permit viewing through the same.

A baffle 86 is mounted in the bore 83 and extends laterally and axially thereof. The baffle 86 can be formed integral with the tip 84 or, alternatively, can be formed of a separate material which is bonded to the tip 84 by suitable means, such as an adhesive. Assuming that the laparoscope 72 is of a type in which the light transmitting capabilities are provided in one semi-circular region of the probe 77 and viewing capabilities are provided in the other semi-circular extremity, the baffle 86 is positioned in such a manner so that it will inhibit, if not prevent light emitted from the distal extremity 78 of the laparoscope from bouncing off of the inner surface of the tip 84 and creating a glare which may obscure vision through the eyepiece 76. In order to prevent the formation of such glare, the baffle 86 is preferably formed of an opaque material, for example a black opaque material. Alternatively, if desired, the baffle 86 can be provided with one surface which is opaque so that light cannot be transmitted through the same to the lower half of the probe 77 so that a clearer field of view is made possible through the cover 81.

A balloon assembly 91 similar to that hereinbefore described is provided. It has a balloon 92 which is cylindrical and elongate, as for example having a generally "hot-dog" shape. The balloon 92 has proximal and distal extremities 93 and 94. As in the previous embodiment, the distal extremity 94 has the capability of being folded inwardly into the interior of the balloon into the proximal extremity of the balloon 93 to reduce its length by approximately one-half and more if desired, by additional inward folding as hereinbefore described in connection with the previous embodiment. Means is provided for securing the balloon 92 to the scope cover 81 and consists of a sleeve 96 (see FIG. 6) extending axially of the balloon 92 for at least a portion of the proximal extremity of the balloon 92 and being secured thereto or formed integral therewith, and encircling the scope cover 81. The sleeve 96 is provided with a weakened region 97 extending the length thereof. The balloon assembly 91 includes means in the form of a tubular member 98 for inflating the balloon 92 in the manner hereinbefore described.

A removable balloon cover 101 is provided which compresses the folded balloon 92 and brings it into close proximity to the scope cover 81. The balloon cover 101 is provided with a weakened region 102 extending the length thereof, and is provided with a finger ring 103 to facilitate removal of the same as hereinafter described.

A skin seal 106 of the type described in Ser. No. 08/267,488 filed Jun. 29, 1994 is provided with a conical surface 107 and an adjoining cylindrical surface 108 which are provided with a continuous helical thread 111. The skin seal is provided with a housing 111 which carries a duckbill valve (not shown) and a axially movable collar 112 which is movable to releasably clamp the skin seal to the scope cover 81.

Operation and use of the balloon dissection apparatus 71 is very similar to the balloon dissection apparatus 11 hereinbefore described. The principal difference in the apparatus and the use of the same is that a laparoscope 72 is continuously available during the introduction of the balloon dissection apparatus 71 into the incision and during movement of the distal extremity of the balloon dissection apparatus 71 into the tissue of the patient, as for example in forming an insufflated anatomic space adjacent a vessel, as for example a saphenous vein. Dissection as hereinbefore explained can be accomplished between the skin of the saphenous vein or, alternatively, on the side of the saphenous vein away from the skin. With dissection taking place on the side of the saphenous vein away from the skin, the light from the laparoscope makes it possible to visually identify externally the saphenous vein location and the side branches by the formation of a silhouette on the skin, thus making it possible to previously locate the necessary incisions and to minimize their size.

The scope cover 81, in addition to providing means permitting viewing by the laparoscope 72, also serves as a tunneling member for creating blunt dissection to permit advancement of the distal extremity of the balloon dissection apparatus 71 along the natural dissection plane of a vessel. Excellent viewing capabilities through the scope cover 81 are made possible because of the baffle inhibiting unwanted reflections within the scope cover 81.

As the balloon 92 is being inflated and unrolled in a distal direction to complete dissection beyond the scope cover 81, this unrolling can be viewed through the laparoscope 72. After the balloon 92 is completely distended and inflated, it can be deflated after which the balloon assembly 91 can be retracted and balloon assembly stripped off of the scope cover 81 by causing separation along the weakened region 97. The skin seal 106 then can be threaded into the incision to form a fluid-tight seal. The laparoscope 72 can then be removed and an inflation device of the type hereinbefore described can be introduced through this skin seal to insufflate the dissected space to create the desired anatomic space adjacent the vessel. Thereafter, the insufflation device can be removed and the laparoscope 72 re-inserted. Alternatively, an operating laparoscope can be inserted to perform the desired procedures alongside the exposed vessel. Alternatively, another incision can be made and the desired surgical procedures can be performed from the other direction while viewing the procedure through the laparoscope already inserted. Thus, it can be seen with the balloon dissection apparatus 71 the advantage which could be obtained with the balloon dissection apparatus hereinbefore described can be obtained, while at the same time making it possible to view the blunt dissection as it takes place by the use of the laparoscope 72 which forms a part of the balloon dissection apparatus 71.

A still further embodiment of the balloon dissection apparatus of the present invention is shown in FIGS. 7, 8 and 9, in which the balloon dissection apparatus 121 is provided which utilizes a laparoscope 72 of the type hereinbefore described. The scope cover 81 hereinbefore described also can be used in connection with the present embodiment.

The principal difference between the balloon dissection apparatus 121 and the balloon dissection apparatus 71 is that a balloon assembly 136 is provided which is carried directly by the scope cover 81 rather than having a separate sleeve being utilized in conjunction with the balloon assembly to secure the same to the scope cover. Thus, as shown in FIG. 7, the balloon assembly 136 consists of a balloon 137 having proximal and distal extremities 138 and 139. As in the previous embodiments, the distal extremity 139 is folded inwardly into the proximal extremity 138 of the balloon 137 until substantially one-half of the balloon is folded into the other half. With the balloon 137 folded in this manner, the distal extremity of the scope cover 81 is inserted into one of the folds as shown in FIG. 7, so that the distal extremity is adjacent one of the folds. The balloon 137 is formed of a transparent material so that viewing through the laparoscope 72 is still possible. Viewing occurs through the distal extremity of the scope cover 81 the folded balloon 137. A balloon cover 146 of the type hereinbefore described, having a longitudinally extending and weakened region 147, can be provided over the balloon to compress the collapsed balloon and to secure the same to the scope cover 81.

Operation and use of the balloon dissection apparatus 121 is very similar to that hereinbefore described. It is readily apparent that viewing of the blunt dissection can be accomplished as the balloon 137 is being advanced into the dissected region. As explained previously, viewing can be accomplished through the balloon 137 because it is substantially transparent, as well as through the transparent distal extremity of the scope cover 81. After the balloon assembly has been inserted, the balloon cover 146 can be removed, and the balloon 137 can be inflated through the tubular member 141. The balloon, upon inflation, will evert in a manner similar to the balloons hereinbefore described until the distal extremity is fully extended as shown in dotted lines in FIG. 7. The balloon 137 will inflate around the scope cover 81 as shown in cross-section in FIG. 7. Viewing can still be accomplished through the laparoscope because of the transparency of the balloon 137.

From the foregoing it can be seen that various types of balloon dissection apparatus can be provided which incorporate the present invention. In those embodiments laparoscopic viewing can be accomplished during the blunt dissection, as well as other surgical procedures to be performed.

What is claimed is:

1. A balloon dissection apparatus for forming an anatomic space alongside an elongate structure in a body, comprising:

a tunneling shaft having proximal and distal extremities;

a flexible elongate cylindrical balloon carried by said tunneling shaft and having proximal and distal extremities, the elongate balloon being circumferentially disposed about said tunneling shaft and being folded inwardly to reduce its length, and having a fully inflated length of greater than said tunneling shaft; and an inflation tube coupled to the balloon for inflating the balloon.

2. Apparatus as in claim 1 wherein said balloon has at least a portion of the distal extremity of the balloon folded inwardly into the balloon to shorten the length of the balloon so that the folded balloon has a folded length which is not substantially greater than the length of the tunneling shaft, the distal folded extremity of the balloon everting and rolling outwardly when the balloon is inflated to provide an inflated balloon having a length greater than the length of the tunneling shaft.

3. Apparatus as in claim 1 together with a balloon cover securing said balloon to said tunneling shaft and to compress the balloon into engagement with the tunneling shaft to facilitate introduction of the balloon into the body.

4. Apparatus as in claim 1 wherein said balloon is formed of a non-elastomeric material.

5. Apparatus as in claim 1 wherein said balloon is formed of a material which is substantially transparent when it is inflated.

6. Apparatus as in claim 1 wherein said tunneling shaft is in the form of an elongate tubular member having a bore therein together with an endoscope disposed in the bore.

7. Apparatus as in claim 6 wherein said tubular member is provided with a closed distal extremity having a rounded tip, said tip being formed of a substantially transparent material.

8. Apparatus as in claim 6 wherein the elongate balloon is folded inwardly to produce at least one fold, and the distal extremity of the tubular member is disposed in said at least one fold of the balloon.

* * * * *